(12) United States Patent
Hamed et al.

(10) Patent No.: US 10,214,858 B2
(45) Date of Patent: Feb. 26, 2019

(54) CELLULOSIC MATERIAL WITH ANTIMICROBIAL AND DEFIBERIZATION PROPERTIES

(71) Applicant: Rayonier Performance Fibers, LLC, Jacksonville, FL (US)

(72) Inventors: Othman A. Hamed, Savannah, GA (US); Romuald S. Krzywanski, Richmond Hill, GA (US)

(73) Assignee: RAYONIER PERFORMANCE FIBERS, LLC, Jacksonville, FL (US)

( * ) Notice: Subject to any disclaimer, the term of this patent is extended or adjusted under 35 U.S.C. 154(b) by 0 days.

(21) Appl. No.: 15/486,390

(22) Filed: Apr. 13, 2017

(65) Prior Publication Data

US 2018/0298559 A1   Oct. 18, 2018

(51) Int. Cl.
| | | |
|---|---|---|
| *D21H 21/36* | (2006.01) |
| *C07C 217/28* | (2006.01) |
| *A61L 15/28* | (2006.01) |
| *C07C 213/08* | (2006.01) |
| *D21H 17/07* | (2006.01) |

(52) U.S. Cl.
CPC .............. *D21H 21/36* (2013.01); *A61L 15/28* (2013.01); *C07C 213/08* (2013.01); *C07C 217/28* (2013.01); *D21H 17/07* (2013.01); *A61L 2300/208* (2013.01); *A61L 2300/404* (2013.01)

(58) Field of Classification Search
CPC ........ D21H 21/36; D21H 17/07; A61L 15/28; C07C 213/08; C07C 217/28
USPC ....................................................... 502/404
See application file for complete search history.

(56) References Cited

U.S. PATENT DOCUMENTS

| | | | |
|---|---|---|---|
| 3,554,862 A | 1/1971 | Hervey |
| 3,677,886 A | 7/1972 | Forssblad |
| 3,809,604 A | 5/1974 | Estes |
| 4,098,996 A | 7/1978 | Ryan et al. |
| 4,144,122 A | 3/1979 | Emanuelsson et al. |
| 4,303,471 A | 12/1981 | Laursen |
| 4,420,484 A | 12/1983 | Gorman et al. |
| 4,432,833 A | 2/1984 | Breese |
| 4,476,323 A | 10/1984 | Hellsten et al. |
| 4,668,273 A | 5/1987 | Haase |
| 4,731,269 A | 3/1988 | Hansen et al. |
| 5,547,541 A | 8/1996 | Hansen et al. |
| 5,858,172 A | 1/1999 | Sears et al. |
| 5,866,242 A | 2/1999 | Tan et al. |
| 6,844,066 B2 * | 1/2005 | Hamed ................... A61L 15/60 428/393 |
| 2004/0229768 A1 | 11/2004 | Blanda et al. |

FOREIGN PATENT DOCUMENTS

| | | |
|---|---|---|
| EP | 0 348 978 | 1/1990 |
| EP | 0 510 619 | 10/1992 |
| JP | 4-17058 | 1/1992 |
| WO | 89/02698 | 4/1989 |
| WO | 91/11977 | 8/1991 |
| WO | 91/12029 | 8/1991 |
| WO | 91/12030 | 8/1991 |
| WO | 94/22501 | 10/1994 |
| WO | 99/06078 | 2/1999 |
| WO | 99/32697 | 7/1999 |
| WO | 01/48025 | 7/2001 |

OTHER PUBLICATIONS

International Search Report dated Jul. 27, 2018 in International Application No. PCT/US18/27287.
Written Opinion of the International Searching Authority dated Jul. 27, 2018 in International Application No. PCT/US18/27287.
Najlaa Z. Al-Ameri et al., "Novel Cationic Gemini surfactants: Preparation, characterization and Breaking of Water-in-Crude Oil Emulsions", International Journal of Applied Chemical Sciences Research, vol. 2, No. 3, Jun. 2014, pp. 1-3, ISSN: 2328-2827 (Online).
Yan Bao et al., "Cationic silicon-based gemini surfactants: Effects of hydrophobic chains on surface activity, physic-chemical properties and aggregation behaviors", Journal of Industrial and Engineering Chemistry 53 (2017) pp. 51-61.

* cited by examiner

*Primary Examiner* — Edward M Johnson
(74) *Attorney, Agent, or Firm* — Wenderoth, Lind & Ponack, L.L.P.

(57) ABSTRACT

The present invention relates to specialty pulp products produced using bifunctional reagents composed of polymeric chain and end caps. The polymeric chain is preferably a polyalkylene glycol based polymer and the end caps are preferably a cationic quaternary ammonium. The bifunctional reagents are especially useful in making specialty fluff with dual functional properties—easy defiberization and antimicrobial properties. The specialty fluff of the present invention prevents odor by inhibiting bacteria growth and production of organic matters, especially when used in an absorbent article intended for body waste management such as baby diapers and adult incontinence device.

20 Claims, 9 Drawing Sheets

PEG-QA
MW = 887.6 g/mol

PEQ-QA
MW = 814.6 g/mol

PPG-QA
MW = 1027.6 g/mol

PPG-QA
MW = 954.6 g/mol

CELLULOSIC MATERIAL WITH ANTIMICROBIAL AND DEFIBERIZATION PROPERTIES

FIELD OF THE INVENTION

The present invention relates to a bifunctional reagent, and use of the reagent to make specialty fluff products from cellulosic material. The specialty fluff of the present invention prevents odor by inhibiting bacteria growth and production of organic matters, especially when used in an absorbent article intended for body waste management such as baby diapers and adult incontinence device.

DESCRIPTION OF RELATED ART

Wood fluff pulps are used in a wide variety of personal care products. These range from absorbent articles such as personal hygiene products to wipes or pads used in medical and food handling applications. While the design of personal care products varies depending upon intended use, there are certain elements or components common to such products. For instance, absorbent articles intended for personal care, such as adult incontinent pads and infant diapers typically are comprised of absorbent core, a top sheet and back sheet. The absorbent core is typically comprised of cellulosic fibers and superabsorbent polymer. Absorbent articles may also include an acquisition-distribution layer located between the top sheet and the absorbent core, to accelerate liquid acquisition times, and reduce product wetness.

In recent years absorbent article designers have shifted their focus to addressing absorbent article bulkiness and skin-wellness issues associated with absorbent article. The skin-wellness issues include the removal of unpleasant odors, and the prevention of skin diseases such as dermatitis, rash and redness caused by wearing a disposable absorbent article for a relatively long time. It is believed that the unpleasant odors in an absorbent article originate from numerous sources including bodily fluids such as urine and menses absorbed by the absorbent articles. Degradation of the components present in these fluids (e.g., protein, fat, etc.) by bacteria can generate malodorous byproducts. In addition, urine and/or other exudates usually contain microorganisms that produce the urease enzyme that is responsible for the degradation of urea present in urine to ammonia. The ammonia, in turn, has the potential to cause dermatitis, rash and/or other forms of skin irritation. For an infant, these conditions can be a serious medical issue.

There have emerged two general categories of absorbent article technologies for removal of odors and improvement of skin wellness: (1) odor absorption technology; and (2) anti-microbial treatment technology. The odor absorption technology includes incorporation into the absorbent article compounds that are known to absorb odors, such as activated carbons, clays, zeolites, silicates, cyclodextrine, ion exchange resins and various mixture thereof as for example described in EP-A-348 978; EP-A-510 619; WO 91/12029; WO 91/11977; WO89/02698; WO 91/12030; WO 94/22501; WO 99/06078; and WO 01/48025 (the contents of each of these applications is incorporated herein by reference in their entirety).

Adsorbent agents control odor by mechanisms where the malodorous compounds and their precursors are physically absorbed by the agents. The agents thereby hinder the exit of the malodorous compounds from absorbent articles. However, such mechanisms are not completely effective because the formation of the odor itself is not prevented, and thus some odor still may be detected in the product. Also, it is believed that the odor absorbing particles lose odor-trapping efficiency when they become moist. Furthermore, in order for these reagents to be effective at controlling odor, a high loading of these reagents is required which increases the cost of the absorbent article, and tends to adversely affect the performance of the absorbent article.

The second category of odor-removal and skin wellness technology involves introducing anti-microbial agents into the absorbent article either by physical or chemical methods. An example of such approach is described in patent WO99/32697 (which is incorporated herein by reference in its entirety), which discloses coating a nonwoven fabric of hydrophobic material (e.g., polypropylene fibers) with an anti-microbial agent chitosan and chitin-based polymers. The anti-microbial agent is applied to the surface of the fabric, and the resulting treated fabric is used as a diaper liner. It is believed, however, that such technology is very limited in preventing odor formation, since the anti-microbial agent is located outside the absorbent core of the absorbent article.

The use of an antimicrobial agent in an absorbent article is also described in Japanese Patent No. 4-17058 (incorporated herein by reference in its entirety). This patent discloses a disposable diaper that is said to prevent the occurrence of diaper rash caused by certain bacteria such as *Colibacillus* and *Candida* and to inhibit the production of ammonia formed by hydrolysis of the urea contained in the urine by bacteria. The disclosed disposable diaper consists of a water-permeable top sheet, a water-impermeable back sheet, and an absorbent layer sandwiched between these sheets. The absorbent layer has an ammonia-adsorbent and an absorbent polymer contains surfactant-based antimicrobial agents such as benzalkonium chloride and/or chlorhexidine gluconate.

It is believed, however, that using surfactant-based antimicrobial agents or bactericides poses some disadvantages. One drawback is that surfactant-based antimicrobial agents tend to reduce the absorbency and the wettability of the absorbent layer. It is also believed that surfactant-based antimicrobial agents are only effective in reducing certain bacterial activity, and have only limited antimicrobial properties.

Regarding the bulkiness of the absorbent articles, in recent years, the thickness of the absorbent articles has been reduced dramatically. For instance, the feminine hygiene pad has been reduced from 15-20 mm in the mid 1980's to about 2.5-6 mm today. Unfortunately, as the products had become thinner, absorbent cores lost integrity. To counter this, absorbent article designers have tried to produce higher integrity cores, such as by compressing the core to a high density and/or use bonding agents to achieve fiber-to-fiber and fiber-to-SAP particle bonding. However, the increased density and increased usage of SAP in these products has caused problems with liquid acquisition and wicking rates. Moreover, compressing the absorbent core to a high density can cause the core to develop hard spots (clusters of SAP and fibers with very high density) that are undesirable to consumers.

In an attempt to overcome these problems, pulp softening approach was adapted by several research groups. Pulp softness is greatly influenced by the degree to which the constituent wood pulp is debonded, i.e., the extent to which hydrogen bonds within the wood pulp are weaken; softer pulps and pulp products typically having decreased hydrogen bonding. Wood pulp softness can be expressed in terms of properties such as Mullen strength (the strength of pulp or a pulp product, measured in kilopascals (kPa), and Kamas energy (the energy required to convert a given amount of pulp or pulp product to a fluff material, measured in watt hours per kilogram (Wh/kg). Lower values of Mullen strength and Kamas energy correlate to softer, increasingly debonded, pulp.

Several method were reported in the literature for pulp softening, among these using cationic surfactants such as those disclosed in U.S. Pat. Nos. 3,554,862; 3,677,886; 3,809,604; 4,144,122; and 4,432,833. Softening agents are usually quaternary ammonium compounds containing one or more fatty groups that soften and lubricate the fibers. When applied to a sheet of wood pulp fibers, the fatty groups disrupt the inter-fiber hydrogen bonding (fiber-to-fiber bonding)—as a result, voids are created among the fibers. These voids enhance the bulk of the fibers, thereby producing a softer and weaker sheet of wood pulp. Similarly, cationic materials such as those disclosed in U.S. Pat. Nos. 3,554,862; 3,677,886; 3,809,604; 4,144,122; and 4,432,833; and nonionic agents such as BEROCELL 587K (manufactured by Akzo Nobel,) also have been used on wood pulp. The use of non-ionic agents, such as fatty acid esters, in combination with cationic retention agents has been disclosed, for example, in U.S. Pat. No. 4,303,471, and it is known to produce good disintegration properties for wood pulp. Unfortunately, the long hydrophobic alkane chains in these softening and debonding agents tend to have undesirable hydrophobic effects on pulps. For example, they tend to decrease the absorbency and wettability of the pulp, thereby rendering it unsuitable for applications such as absorbent articles, where high absorbency and fast wicking are desirable. Reductions in absorbent properties using surfactant for debonding can be quite substantial (e.g., 18% reductions for a partially debonded southern bleached kraft pulp and about 27% reductions for a fully debonded southern bleached kraft pulp). Moreover, the softened and de-bonded fluff pulps tend to form more hard spots than conventional untreated fluff pulp when calendared with SAP particles.

Another proposed solution for improving softness is to use mercerized fibers. The use of mercerized fibers to enhance the softness of the absorbent cores has been disclosed in U.S. Pat. No. 5,866,242. However, these fibers are very expensive when compared to non-mercerized fibers.

As an alternative to the use of additives or mercerized fibers, plasticizing agents such as those disclosed in U.S. Pat. Nos. 4,098,996; 5,547,541; and 4,731,269 also have been used as a softener for wood pulp. Typically, a plasticizing agent is added to a pulp slurry prior to forming wet-laid sheets. The plasticizing agent is added in large quantities of at least 10 weight % of pulp. The resulting pulp sheet usually lacks stiffness, and it is easy to densify when air-laid to a nonwoven pad. Common plasticizing agents include polyhydroxy compounds such as glycerol; and other polyhydroxy compounds. Ammonia, urea, and alkylamines are also known to plasticize wood pulp (see A. J. Stamm, FOREST PRODUCTS JOURNAL 5(6):413, 1955).

Nonionic reagents such as alkyl ester were also used to debond pulp in the paper industry (e.g. triacetin, U.S. Pat. No. 5,858,172) but even they cause minor adverse effects on absorbency. It is believed that pulp treated with triacetin is not suitable for use in absorbent articles intended for body waste management, since they tend to degrade and release acetic acid.

Accordingly, it would be desirable to provide a method of treating pulp to form fluff pulp with improved softness and reduced inter-fiber bonding without sacrificing the absorbent properties of the pulp.

Based on the foregoing, there remains a need in the art for softwood pulp with low values of Mullen strength and Kamas energy. A need also exists for a fluff that inhibits odors caused by the growth of bacteria present in bodily-fluids, where the fluff has activity toward a wide range of bacteria, and is capable of maintaining odor-inhibiting activity over extended periods.

A novel material in this regard would be one with dual functional: soften the fluff pulp and add to it antimicrobial characteristics.

SUMMARY OF THE INVENTION

In view of the difficulties presented in making soft pulp and adding antimicrobial characteristics to it, there remains a need for relatively inexpensive, softening agent suitable for making soft fluff pulp without scarifying absorbency and liquid transport properties of the fluff pulp. A need also exist for antimicrobial agent that forms with the fluff pulp a structure capable of inhibiting odors caused by the growth of bacteria present in bodily fluids and is capable of maintaining odor-inhibiting activity over extended periods.

It therefore is a feature of the embodiments described herein to provide a simple, relatively inexpensive bifunctional reagent suitable for making a dual functional pulp that is soft and has antimicrobial properties. It also is a feature of the embodiments to provide a process for making the bifunctional reagent. It also is a feature of the embodiments to provide a process for making the dual functional fluff pulp.

The embodiments described herein desire to fulfill these needs and to provide further related advantages, that will be readily appreciated by those skilled in the art.

The present invention desires to fulfill these needs and to provide further related advantages, although the invention is not limited solely to methods, and materials that fulfill these or other needs.

The present invention relates to specialty pulp products produced using bifunctional reagents composed of polymeric chain and end caps. The polymeric chain is a polyalkylene glycol based polymer and the end caps are cationic quaternary ammonium. The bifunctional reagents are especially useful in making specialty fluff with dual functional properties—easy defiberization and antimicrobial properties.

The bifunctional reagent can be made from reacting a polyalkylene glycol diglycidyl ethers with dimethylalkyl amines. Embodiments of the present invention also relate to methods of using the bifunctional reagent for making the specialty fluff pulp of the present invention. The specialty fluff of the present invention prevents odor by inhibiting bacteria growth and production of organic matters, especially when used in an absorbent article intended for body waste management such as baby diapers and adult incontinence device.

More specifically, the present invention provides a bifunctional reagent comprising a reaction product of an alkyl amine and an epoxide. The epoxide may be a polyglycidyl ether. The polyglycidyl ether may be selected from the group consisting of ethylene glycol diglycidyl ether, glycerol triglycidyl ether, glycerol diglycidyl ether, glycerol propoxylate triglycidyl ether, polyethylene glycol diglycidyl ether, propylene glycol diglycidyl ether, polypropylene glycol diglycidyl ether, 1,4-cyclohexanoldimethanol diglycidyl ether, diglycidyl 1,2-cyclohexanedicrboxylate, N,N-diglycidyl aniline, N,N-diglcidyl-4-glycidyloxyaniline, and diglycidyl 1,2,3,4-tetrahydrophthalate.

The polyglycidyl ether may be an alkylene glycol diglycidyl ether. The alkylene glycol diglycidyl ether may be ethylene glycol diglycidyl ether, polyethylene ethylene glycol diglycidyl ether, propylene glycol diglycidyl ether, polypropylene glycol diglycidyl ether or a combination of thereof.

The alkyl amine may have the formula $NR_1R_2R_3$, where $R_1$ and $R_2$ are hydrogen or alkyl groups having 1 to 2 carbon atoms or a mixture of thereof and $R_3$ is an alkyl group having 1 to 30 carbon atoms, and wherein the alkyl group $R_3$ may be saturated, unsaturated, substituted, un-substituted, branched, un-branched, cyclic, and/or acyclic, and may contain 1 to 3 heteroatoms.

The bifunctional reagent may have the following chemical structure:

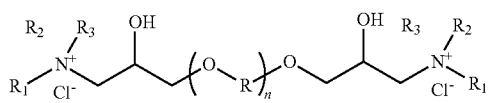

wherein n is an integer from 1 to 1,000, and preferably n is 1 to 100;

R is ethyl, isopropyl or butyl;

$R_1$ and $R_2$ can be the same or different and are selected from hydrogen, methyl, or ethyl; and $R_3$ is an alkyl group with 3 to 30 carbon atoms, which alkyl group may be saturated, unsaturated, substituted, un-substituted, branched, un-branched, cyclic, and/or acyclic, and may contain 1 to 3 heteroatoms.

The alkylene glycol diglycidyl ether may be a polyalkylene glycol diglycidyl ether selected from a combination of polyethylene glycol diglycidyl ether, polypropylene glycol diglycidyl ether and polytetrahydrofuran or a mixture of thereof. The polyalkylene glycol diglycidyl ether may have a molar mass in a range of 312 g/mol to 10,000,112 g/mol.

The alkyl amine may be selected from N,N-Dimethylethylamine, N,N-Dimethylpropyl, amine, N,N-Dimethylbutylamine, N,N-Dimethylpentylamine, N,N-Dimethylhexylamine, N,N-Dimethyloctylamine, N-methyl-n-octyl amine and n-octylamine.

The bifunctional reagent is preferably soluble or forms a suspension in water.

The polyalkylene glycol diglycidyl ether and the alkyl amine are preferably reacted in a ratio of 1:0.1 to 1:2 molar equivalents.

Also provided is a cellulose composition, comprising cellulose fibers and about 0.01 wt. % to about 1.0 wt. % of the bifunctional reagent of the invention. The cellulose composition preferably has antimicrobial activity. The cellulose composition, when dosed with a bacteria suspension, preferably reduces the number of bacteria by more than 95% within a period of 24 hr. The cellulose composition, when dosed with a bacteria suspension, preferably prevents bacteria growth for up to about 36 hours. The cellulose composition is preferably effective against bacteria which is gram positive or gram negative. Preferably, the composition exhibits antimicrobial activity against *Proteus mirabilis, Staphylococcus aureus, Klebsiella pneumonia* or *E. coli*.

The cellulose composition having 0.1 wt. % bifunctional reagent preferably has a Kamas energy which is reduced at least 15% compared to the Kamas energy of a cellulose composition without the bifunctional reagent. The cellulose composition having 0.1 wt. % bifunctional reagent preferably has a Kamas energy which is reduced at least 25% compared to the Kamas energy of a cellulose composition without the bifunctional reagent.

The cellulose composition having 0.1 wt. % bifunctional reagent in sheet form with a 100 gsm preferably has a burst index which is reduced by at least 15% compared to the burst index of a cellulose composition without the bifunctional reagent. The cellulose composition having 0.25 wt. % bifunctional reagent in sheet form with a 100 gsm preferably has a burst index which is reduced by at least 25% compared to the burst index of a cellulose composition without the bifunctional reagent.

Also provided is an absorbent article of manufacture, comprising the cellulose composition of the invention. The absorbent article may be a diaper, an incontinent device, a feminine hygiene product, a wipe, a bandage, a bed pad, or any combination thereof.

Further provided is a method for making a bifunctional reagent, which comprises:
 a. providing polyalkylene glycol diglycidyl ether;
 b. providing an alkyl amine compound;
 c. mixing the polyalkylene glycol diglycidyl ether and the alkyl amine in 1:2 equivalent;
 d. stirring the mixture to obtain a product; and
 e. neutralizing the product with HCl to a pH of 1.5 to 7.0, to produce a polyalkylene glycol based cationic quaternary ammonium.

Additionally, there is provided a method for making a cellulose composition, which comprises:
 (a) providing an aqueous solution of the bifunctional reagent;
 (b) providing a cellulosic fiber in sheet, roll, mat or fluff form; and
 (c) impregnating the cellulosic fiber with the aqueous solution of the bifunctional reagent.

The impregnation may be carried out by suspending the cellulosic fiber in a solution of the bifunctional reagent. The impregnation may be carried out by spraying, dipping, rolling, or applying with a puddle press, size press or a blade-coater.

DETAILED DESCRIPTION OF INVENTION

Figure 1:
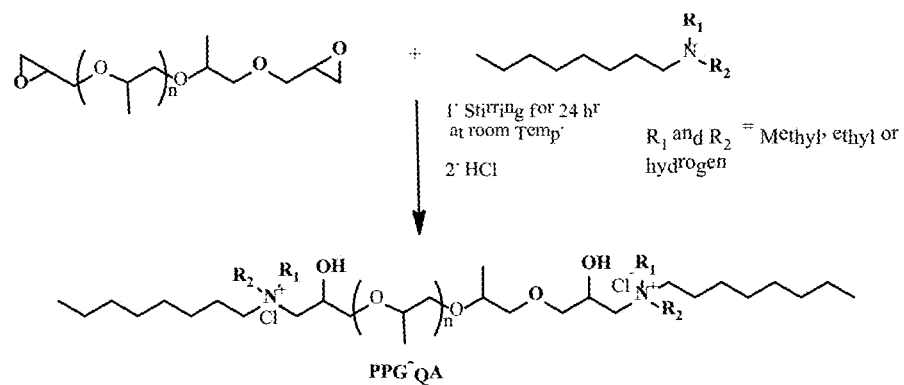
FIG. 1 shows a reaction scheme for making polypropylene glycol based cationic quaternary ammonium and its interaction with cellulose chains.
Figure 1:
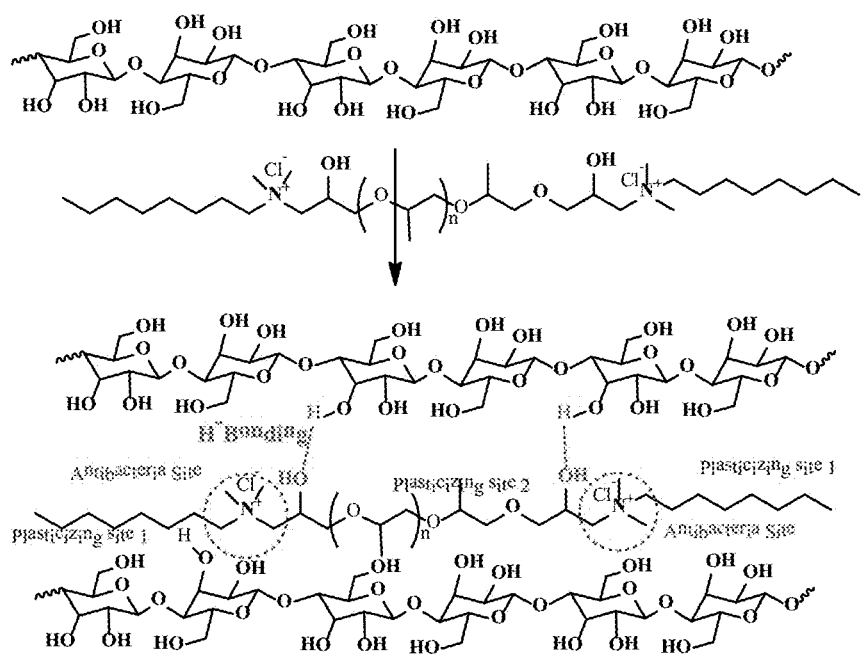

The invention relates generally to cellulosic fibers with dual properties—soft and having antimicrobial activities. The cellulosic fibers are in sheet or fluff form.

The cellulosic fibers made in accordance with the present invention are especially suited for use in absorbent articles intended for body waste management. One advantage of using the cellulosic fiber of the present invention in absorbent article is that the fiber has the ability to eliminate or suppress the growth of microorganisms present in bodily fluids that are accountable for the breakdown of urea into ammonia. The resultant absorbent article is substantially odor-free. The absorbent article made from the pulp of the present invention is expected to be soft, flexible and free of hard spots caused by superabsorbent polymer.

Throughout this description, the terms "impregnated" or "impregnating" insofar as they relate to a solution of the bifunctional reagent impregnated in a fiber, denote an intimate mixture of the solution of the bifunctional reagent and cellulosic fluff pulp, whereby the bifunctional reagent may be adhered to the fibers, adsorbed on the surface of the fibers, or linked via covalent, hydrogen or other bonding (e.g., Van der Waals forces) to the fibers.

As used herein, the phrase "odor-inhibiting" refers to the ability of an agent, fiber, or the like, to reduce number of bacteria and thus prevent, inhibit, or eliminate odor. The cellulosic fibers of the embodiments are useful in absorbent articles, and in particular, are useful in forming absorbent cores of absorbent articles. The particular construction of the absorbent article is not critical to the embodiments, and any absorbent article can benefit from the embodiments. Suitable absorbent garments are described, for example, in U.S. Pat. Nos. 5,281,207, and 6,068,620, the disclosures of each of which are incorporated herein by reference in their entirety including their respective drawings. Those skilled in the art will be capable of utilizing cellulosic fibers of the embodiments in absorbent garments, cores, acquisition layers, and the like, using the guidelines provided herein.

As used herein, the expression "cellulosic fibers" refer to those fluff pulps that are conventionally employed for use in absorbent articles. Any cellulosic fluff pulp can be used, so long as it provides the physical characteristics of the fibers described herein. Suitable cellulosic fluff pulps for use in the embodiments include those derived primarily from wood pulp. Suitable wood pulp can be obtained from any of the conventional chemical processes, such as the kraft and sulfite processes. Preferred fibers are those obtained from various soft wood pulp such as southern pine, white pine, Caribbean pine, western hemlock, various spruces, (e.g. black spruce or sitka spruce), Douglas fir or mixtures and combinations thereof. Fibers obtained from hardwood pulp sources, such as gum, maple, oak, eucalyptus, poplar, beech, and aspen, or mixtures and combinations thereof also may be used, as well as other cellulosic fiber derived from cotton linter, bagasse, kemp, flax, and grass. The cellulosic fiber can be comprised of a mixture of two or more of the foregoing cellulose pulp products. Particularly preferred fibers for use in the embodiments are those derived from wood pulp prepared by the Kraft and sulfite-pulping processes.

The cellulosic fibers used in the present invention described herein also may be pretreated prior to use. This pretreatment may include physical treatment such as subjecting the fibers to steam, caustic, cross-linked, chemical treatment or CTMP (chemi-thermomechanical pulp treatment).

The expression "pulp sheet" as used herein refers to cellulosic fiber sheets formed using a wet-laid process. The sheets typically have a basis weight of about 200 to about 800 gsm and density of about 0.3 g/cc to about 1.0 g/cc. The pulp sheets are subsequently defiberized in a hammermill to convert them into fluff pulp before being used in an absorbent product.

In accordance with embodiments of the present invention, the bifunctional reagents of the present invention are made by reacting an alkyl amine and an epoxide then neutralizing the product to a pH 7.0 or lower with diluted acid. Upon neutralization with an acid forms polypropylene glycol based quaternary ammonium salts. Without being bound to any theory, the polypropylene glycol and the n-octyl groups disrupt the inter-fiber hydrogen bonding (plasticizing sites), as a result, voids are created among the fibers. As a result of that soft pulp with reduced defiberization energy is produced.

Preferably the alkyl amine has the formula $NR_1R_2R_3$, where $R_1$ and $R_2$ are hydrogen, methyl, ethyl or a combination of thereof and $R_3$ is an alkyl group with three carbons and more. Preferably $R_3$ is an alkyl group with 30 carbons or lower, more preferably $R_3$ group contains number of carbons that form water soluble bifunctional reagent. Most preferably $R_3$ is an alkyl group with 12 carbons or lower. The alkyl group may include saturated, unsaturated (e.g., alkenyl, alkynyl, allyl), substituted, un-substituted, branched, un-branched, cyclic, and/or acyclic compounds. Examples on trialkylamines but not limited to are: N,N-Dimethylethylamine, N,N-Dimethylpropyl, amine, N,N-Dimethylbutylamine, N,N-Dimethylpentylamine, N,N-Dimethylhexylamine N,N-Dimethyloctylamine, N-methyloctylamine and octylamine Any epoxide that forms water soluble cationic quaternary ammonium bifunctional reagent upon reaction with alky amine described above could be suitable for use in the present invention. The epoxide preferably is a polyepoxide: including ethylene glycol diglycidyl ether, glycerol triglycidyl ether, glycerol diglycidyl ether, glycerol propoxylate triglycidyl ether, polyethylene glycol diglycidyl ether, propylene glycol glycidyl ether, polypropylene glycol diglycidyl ether, 1,4-cyclohexanoldimethanol diglycidyl ether, diglycidyl 1,2-cyclohexanedicrboxylate, N,N-diglycidyl aniline, N,N-diglcidyl-4-glycidyloxyaniline, and diglycidyl 1,2,3,4-tetrahydrophthalate; and polyfunctional epoxy silanes.

The bifunctional reagent more preferably is polyalkylene glycol based cationic quaternary ammonium that is produced form reacting alky amine with polyalkylene glycol diglycidyl ether, examples of the polyalkylene glycol diglycidyl ether compounds suitable for use in embodiments of the present invention but not limited to are polyethylene glycol diglycidyl ether, polypropylene glycol diglycidyl ether, and polytetrahydrofuran diglycidyl ether or any combination thereof.

The molar mass of polyalkylene glycol diglycidyl ether could be anywhere from 307 g/mol to 10,000,099 g/mol.

A representative example for making polyalkylene glycol based cationic quaternary ammonium salt and its interaction with cellulose chains is shown in FIG. 1. As shown in FIG. 1, the amine makes a nucleophile addition on the epoxy groups to produce a polymeric product with triple moieties: polyalkylene glycol back bone with two hydroxyl groups and end capped with cationic quaternary amines which upon neutralization with acid forms quaternary ammonium salts. The polypropylene glycol and the alkyl (n-octyl) groups disrupt the inter-fiber hydrogen bonding (plasticizing sites), as a result, voids are created among the fibers.

The bifunctional reagent may be prepared by any suitable and convenient procedure. The polyalkylene glycol diglycidyl ether and trialkyl amine are generally reacted in a mole ratio of polyalkylene glycol diglycidyl ether to trialkyl amine of about 1:0.1 to about 1.0:2.0. Preferably the reaction is carried out in the presence of small amount of water or other organic solvent that acts as diluent and a catalyst at a weight ratio of reactant to solvent from 1:0.1 to 1:10, preferably from 1:0.2 to 1:1. Useful organic solvents include but are not limited to: tetrahydrofuran, N,N-dimethyl acetamide, N,N-dimethyl formamide, isopropyl alcohol, t-butyl alcohol, polyethylene glycol, and polypropylene glycol.

The reaction may be carried out within the temperature range of room temperature up to 120° C. Preferably the reaction is carried out at about 60° C. for about 4 hours, more preferably for about 12 hours and most preferably for about 24 hours. More preferably the reaction is carried out at room temperature for about 4 hours, more preferably for about 12 hours and most preferably for about 24 hours. The product of the reaction is water-soluble or partially water soluble, and can be diluted with water to any desirable concentration.

Optionally, a catalyst may be added to the solution to accelerate the reaction between the polyalkylene glycol diglycidyl ether and alkyl amine. Any catalyst known in the art to accelerate the formation of a covalent linkage between the two materials could be used in embodiments of the present invention. Preferably, the catalyst is a Lewis acid selected from aluminum sulfate, magnesium sulfate, and any Lewis acid that contains at least a metal and a halogen, including, for example $FeCl_3$, $AlCl_3$, $TiCl_4$ and $BF_3$.

In one embodiment, the bifunctional reagent is applied to the cellulose fibers in an aqueous solution. Preferably, the aqueous solution has a pH from about 2.5 to about 7.0.

Any method known in the literature for making quaternary ammonium salts could be used in accordance with the present invention for making polyalkylene glycol diglycidyl ether based quaternary ammonium salts. Like for instance, polyalkylene glycol diglycidyl ether could be first reacted with dialkylamine or an alkyl amine to form polyalkylene glycol trialkylamine or dialkylamine based polymer, respectively, then reacted with alkyl halide to form the bifunctional reagent of the present invention. Useful alkyl halide for use in the present invention are methyl or ethyl halide where the halide is chloro, bromo, and iodo. Examples of alkyl halide useful for use in the present invention but not limited to are: methyl iodide, methyl chloride, methyl bromide, ethyl chloride, ethyl bromide and ethyl iodide.

Useful dialkyl amines for use in the present invention are those with the formula $NHR_1R_2$, where $R_1$ is alkyl groups having 1 to 2 carbon atoms and $R_2$ is an alkyl group with one carbons and more. Preferably $R_2$ is an alkyl group with 30 carbons or lower, more preferably the $R_2$ group contains a number of carbons that form a water soluble reagent of polyalkylene glycol based cationic quaternary ammonium salt. Most preferably $R_2$ is an alkyl group with 12 carbons or lower. The alkyl group may include saturated, unsaturated (e.g., alkenyl, alkynyl, allyl), substituted, un-substituted, branched, un-branched, cyclic, and/or acyclic compounds. Examples of dialkyamines useful for in the present invention but not limited to are: N-methylethylamine, N-methylpropylamine, N-methylbutylamine, N-methylpentylamine, N-methylhexylamine, N-methyloctylamine. The reaction between polyalkylene glycol diglycidyl ether and an alky (polypropylene glycol diglycidyl ether) and dialkylamine could be carried out in an organic solvent or in water, preferably it in water. The reaction between alkylhalide and polyalkylene glycol trialkylamine polymer preferably is carried out in organic solvent. Any organic solvent known in the art that does not react with the epoxy or the amine groups could be used in the present invention. Useful solvents include but are not limited to: tetrahydrofuran, N,N-dimethylacetamide, N,N-dimethylformamide, isopropyl alcohol, t-butyl alcohol, polyethylene glycol, and polypropylene glycol.

Preferably the bifunctional reagent, after being prepared, is diluted with water to a concentration sufficient to provide an effective amount of bifunctional reagent on pulp. The solution of the bifunctional reagent can be added to the pulp so that a predetermined amount of the bifunctional reagent is provided to the fiber. In other words, the effective amount of the bifunctional reagent to be added to the pulp depends upon the concentration of the bifunctional reagent in the solution. Using the guidance provided herein, one of ordinary skill in the art will be able to determine how much of the bifunctional reagent solution to add to the pulp to provide the desired amount of the bifunctional reagent to the fiber.

The expression "effective amount" as used herein is defined as a level sufficient to prevent growth of bacteria present in urine, for a predetermined period of time and soften the pulp. After application of the solution of the bifunctional reagent to the fiber, the bifunctional reagent preferably is present on the fiber in an amount of about 0.001 wt. % to 10.0 wt. % based on the fiber weight. More preferably, the bifunctional agent is present in an amount of about 0.002 wt. % to about 5.0 weight %, even more preferably present in an amount of about 0.003 wt. % to about 2.0 wt. %, even more preferably present in an amount of about 0.005 wt. % to about 1.0 wt. %. By way of example, 1 wt. % of bifunctional reagent means 1.0 g of the bifunctional reagent per 100 g oven dried pulp.

Another aspect of the present invention provides a process for making dual function pulp by treating cellulosic fibers with a solution of bifunctional reagent of the present invention. The process preferably comprises treating cellulose fibers in sheet, roll or fluff form with an aqueous solution containing the bifunctional reagents, followed by drying at sufficient temperature and for a sufficient period of time to a moisture content not higher than 10%. In another aspect of the invention, the fibers can be in a mat of non-woven material. Fibers in mat typically have a lower basis weight than fibers in the sheet form. In yet another feature of an embodiment of the invention, the fibers can be used in the wet or dry state.

Any method of applying the bifunctional reagent to the fibers may be used. Any method that leads to formation of an intimate mixture of a bifunctional reagent and cellulosic fibers could be used, whereby the bifunctional reagent may be adhered to the fibers, adsorbed on the surface of the fibers, or linked via chemical, hydrogen or other bonding (e.g., Van der Waals forces) to the fibers. Acceptable methods include, for example, suspending, spraying, dipping, impregnation, and the like.

In the case where pulp in fluff form is used, preferably the pulp is slurried in a solution of the bifunctional reagent(s), pressed to a desired pick-up that affords desired amount of bifunctional reagents on pulp then sheeted. Fiber in sheet form preferably impregnated with a solution of the bifunctional reagent, impregnation creates a uniform distribution of the bifunctional reagent on the sheet and provides better penetration of the bifunctional reagent into the interior part of the fibers. Fibers in the roll form are conveyed through a treatment zone where the bifunctional reagent is applied by conventional methods such as spraying, rolling, dipping, knife-coating or any other manner of impregnation. A preferred method of applying the aqueous solution containing the bifunctional reagent to fibers in the roll form is by puddle press, size press, or blade coater.

Figure 2:
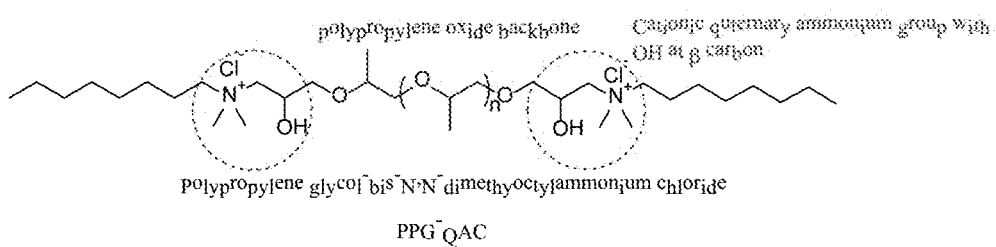
FIG. 2 shows the chemical structure of one embodiment of the bifunctional reagent of the present invention and shows the unique bifunctionality of the reagent.

One benefit of the embodiments described herein is that the resultant cellulosic fibers exhibit excellent anti-microbial properties. Quaternary ammonium compounds with known antimicrobial activities are only effective toward gram negative bacteria. Surprisingly, it was found the bifunctional reagent (polyalkylene glycol based cationic quaternary ammonium) of the present invention is novel and has excellent activity toward both gram positive and gram negative bacteria. Without bounding to a theory, the excellent activity of the bifunctional reagents of the present invention could be related to the unique functionality present in its chemical structure as shown by one embodiment in FIG. 2. The structure composed of three unique functionalities polyalkylene glycol end capped with cationic quaternary ammonium with a hydroxyl group at β-carbon.

Preferably, the dual functional fiber of the various embodiments continues to exhibit acceptable anti-microbial activity after 24 hours, more preferably the fiber continues to exhibit acceptable anti-microbial activity after 36 hours. As used herein, "acceptable" anti-microbial activity means capability of the fiber to reduce the populations of microorganisms, such as those present in urine, or prevent the growth of the organism by at least 96%. Preferably, the dual functional fiber decreases the microorganisms by at least about 98.0%, and more preferably by at least about 99.5%. By the elimination of the microorganism or by inhibiting the growth of the organism by more than 99.5% the reduction of odor in the absorbent article is observed.

In one embodiment, the dual pulp of the present invention when inoculated with a 1.0 mL suspension of test organism of *Staphylococcus aureus* (gram positive) and allowing the inoculum to completely absorb into the pulp, preferably the bacteria count is reduced by 99.0% in 24 hr, more preferably by 99.5% and most preferably by 99.9%.

In another embodiment, the dual pulp of the present invention when inoculated with a 1.0 mL suspension of test organism of *Klebsiella pneumonia* or *Escherichia coli* (gram negative) and allowing the inoculum to completely absorb into the pulp, preferably the bacteria count is reduced by 99.0% in 24 hr, more preferably by 99.5% and most preferably by 99.9%.

Further, the dual functional reagent was found to act as a pulp softener. It was found that when the bifunctional reagent of the present invention is applied to the pulp it reduces the burst index and the Kamas energy of the pulp without affecting pulp classifications and absorbency.

The term "softened pulps" refers to the pulp treated with the bifunctional reagent during or after the sheet forming which makes the pulp sheet softer and easier to fluff or defiber. As a results of that, Burst and Kamas energy of the sheet are substantially reduced.

"Burst" refers to the air pressure in kilopascals (kPa) required to rupture a sheet of pulp under certain experimental conditions. Burst determined on some of the products presented in the examples using a method based on TAPPI T 403. The test was conducted on sheets with circular shape and basis weights of about 100 gsm (diameter=15.8 cm). T807. A TMI Monitor Burst 1000 is used to measure the air pressure required to rupture a pulp sheet. Mullen strength is recorded as kPa at rupture.

"Kamas energy" is the energy (Wh/kg) required to convert a given amount of pulp in sheet form to a fluff form. A hammer mill Model H-01-C was used to defiberize sheets of the present invention presented in the examples. In determining the Kamas energy a strips of pulp sheets 5 cm wide were fed into the hammer mill, using 4200 rpm motor speed, 50% feeder speed, and an 8 mm screen. The energy required to defiberize the pulp sheet is recorded in Wh/kg.

In light of the examples discussed shown below, and the data contained therein, the present invention provides a dual functional pulp wherein the Kamas energy in Wh/kg of the pulp preferably reduced by 10%, more preferably is reduced by 20% and most preferably was reduced by 30% Wh/kg or more.

Further, the present invention provides a dual functional pulp wherein the Burst Index of the pulp preferably is reduced by 25%, more preferably by 30%, even more preferably by 35%.

The term "absorbency" refers to the total capacity, absorbency under load and retention under centrifuge of treated pulp. "Without affecting the absorbency of pulp" herein means the absorbency of the treated pulp is similar to that of untreated pulp or higher as determined by Hanging Cell Test method.

Moreover, the absorbent capacity, the absorbency under load and the centrifuge retention of the pulp of the present invention preferably are similar to those of untreated pulp.

In another embodiment, the specialty dual functional pulp of the present invention fibers insulted with bacterial suspension of *Proteus mirabilis* in urine preferably maintains a pH of less than about 8.5 for up to 36 hours. More preferably, the odor-inhibiting fibers insulted with bacterial suspension of *Proteus mirabilis* in urine maintain a pH of less than about 8.0, and most preferably maintain a pH not lower than 5 and not higher than 7.0. Maintenance of the pH of the absorbent article in the range of 5.0 to 7.0 reduces the tendency of the wearer to develop skin irritation and rashes.

Absorbent articles contain the specialty pulp made in accordance with the embodiments reduce the growth of bacteria and other microbes, such as those present in urine and other bodily fluids, thus preventing infections and reducing the discomfort of the wearer. The specialty dual functional pulp made according to the embodiments provide anti-microbial characteristics and odor control properties that are beneficial in various absorbent articles. Examples of absorbent articles include without limitation diapers, training pants, swim wear, absorbent underpants, baby wipes, adult incontinence products, feminine hygiene products, and the like. The specialty pulp made according to the embodiments also provide anti-microbial characteristics and odor control properties to various medical absorbent articles include, without limitation, garments, under pads, absorbent drapes, bandages, and medical wipes.

The specialty pulp of the present invention of the embodiments is particularly useful in an absorbent core used in absorbent articles intended for personal care applications, such as diapers, feminine hygiene products or adult incontinence products. The phrase "absorbent core" as used herein generally refers to a matrix of cellulosic fibers with superabsorbent material disposed amongst fibers. The absorbent core may comprise about 10 weight % to about 100 weight % specialty pulp, based on the total weight of the absorbent core.

The specialty pulp of the present invention can be used alone in the absorbent core or in combination with conventional fibers. Any conventional cellulosic fiber may be used, including any of the wood fibers mentioned herein, caustic-treated fibers, rayon, cross-linked fibers, cotton linters, and mixtures and combinations thereof.

Any cross-linked fibers known in the art could be used in the embodiments. Exemplary of cross-linked fibers include cellulosic fibers cross-linked with compounds such as formaldehyde or its derivatives, glutaraldehyde, epichlorohydrin, methylated compounds such as urea or urea derivatives, dialdehydes such as maleic anhydride, non-methylated urea derivatives, polycarboxylic acids or polymeric polycarboxylic acids such as citric acid, polymaleic acid or other such compounds. For example, suitable cross-linked fibers are described in U.S. Patent Publication No. 20050079361A1, the disclosure of which is incorporated herein by reference in its entirety.

An absorbent core having odor-inhibiting fibers may be obtained may be obtained, as described above, using conventional fluff pulp fiber, and thereafter applying the odor-inhibiting formulation to the post-manufactured absorbent core. In this embodiment, the application of the odor-inhibiting formulation may be performed, for example, by spraying, rolling, and/or printing the odor-inhibiting formulation onto the web of absorbent core material, or onto individualized absorbent cores that have been prepared from the web of absorbent core material.

In order that the various embodiments may be more fully understood, the invention will be illustrated, but not limited, by the following examples. No specific details contained therein should be understood as a limitation to the embodiments except insofar as may appear in the appended claims.

Test Methods:

Percent Reduction in Bacteria

The tests were performed by Biosan Laboratories, Inc. in. Warren, Mich.

In this test a sample of pulp is cut to circles with a diameter of 4.8±0.1 cm. Pulp samples were placed in sterile empty specimen cups and inoculated with a 1.0 mL suspension of test organism, allowing the inoculum to completely absorb into the pulp. Each sample was incubated for the specific contact time, then transferred to a 10 mL volume of neutralizing solution and vigorously shaken by vortex. The resulting suspension was inoculated to media supportive of bacterial growth and incubated at 36±2° C. for 18-24 hours and the colonies of surviving bacteria were counted. At each designated time point, the process was repeated. The test was performed on three organisms *Pseudomonas aeruginosa*, *Staphylococcus aureus*, and *Escherichia coli* (*E-Coli*)

$$\% \text{ Reduction} = \frac{\text{Control (cfu/mL@ T = 0)} - \text{(Sample cfu/mL@ T = time point)}}{\text{Control (cfu/mL@ T = 0)}} \times 100$$

Hanging Cell Test Method

The absorbency test method was used to determine the absorbency under load, free swell, and retention after centrifuge. The test was carried out in a one inch inside diameter plastic cylinder having a 100-mesh metal screen adhering to the cylinder bottom "cell," containing a plastic spacer disk having a 0.995 inch diameter and a weight of about 4.4 g. In this test, the weight of the cell containing the spacer disk was determined to the nearest 0.001 g, and then the spacer was removed from the cylinder and about 0.35 g (dry weight basis) of cellulosic based acquisition fibers were air-laid into the cylinder. The spacer disk then was inserted back into the cylinder on the fibers, and the cylinder group was weighed to the nearest 0.001 g. The fibers in the cell were compressed with a load of 4.0 psi for 60 seconds, the load then was removed and fiber pad was allowed to equilibrate for 60 seconds. The pad thickness was measured, and the result was used to calculate the dry bulk of cellulosic based acquisition fibers.

A load of 0.3 psi was then applied to the fiber pad by placing a 100 g weight on the top of the spacer disk, and the pad was allowed to equilibrate for 60 seconds, after which the pad thickness was measured, and the result was used to calculate the dry bulk under load of the cellulosic based acquisition fibers. The cell and its contents then were hanged in a Petri dish containing a sufficient amount of saline solution (0.9% by weight saline) to touch the bottom of the cell. The cell was allowed to stand in the Petri dish for 10 minutes, and then it was removed and hanged in another empty Petri dish and allowed to drip for about 30 seconds. The 100 g weight then was removed and the weight of the cell and contents was determined. The weight of the saline solution absorbed per gram fibers then was determined and expressed as the absorbency under load (g/g). The free swell of the cellulosic based transfer fibers was determined in the same manner as the test used to determine absorbency under load above, except that this experiment was carried using a load of 0.01 psi. The results are used to determine the weight of the saline solution absorbed per gram fiber and expressed as the absorbent capacity (g/g).

The cell then was centrifuged for 3 min at 1400 rpm (Centrifuge Model HN, International Equipment Co., Needham HTS, USA), and weighed. The results obtained were used to calculate the weight of saline solution retained per gram fiber, and expressed as the retention after centrifuge (g/g).

Fiber Quality

Pulp fiber quality evaluations (fiber length, kink, curl, and fines content) were carried out on an OpTest Fiber Quality Analyzer (OpTest Equipment Inc., Waterloo, Ontario, Canada) and Fluff Fiberization Measuring Instruments.

Fluff Fiberization Measuring Instrument (Model 9010, Johnson Manufacturing, Inc., Appleton, Wis., USA) was used to measure knots, nits and fines contents of fibers. In this instrument, a sample of fibers in fluff form was continuously dispersed in an air stream. During dispersion, loose fibers passed through a 16 mesh screen (1.18 mm) and then through a 42 mesh (0.36 mm) screen. Pulp bundles (knots) which remained in the dispersion chamber and those that were trapped on the 42-mesh screen were removed and weighed. The formers are called "knots" and the latter "accepts." The combined weight of these two was subtracted from the original weight to determine the weight of fibers that passed through the 0.36 mm screen. These fibers were referred to as "fines."

PREPARATION EXAMPLES

This example illustrates representative methods for making the bifunctional reagent and the specialty fluff.

Preparation of Bifunctional Reagent Polyethylene Glycol Based Cationic Quaternary Ammonium (PEG-QA).

To polyethylene glycol diglycidyl ether (110.0 g, 0.22 mol, MW of PEGDGE=500 g/mol)) in around bottom flask (500 mL) was added N,N-dimethyl-n-octylamine (0.4 mol, 62.8 g). After mixing for about 30 min, water (100.0 mL) was as added to the mixture. A mild exothermic reaction was started after a few min after the addition of water. The mixture was stirred overnight at room temperature. A clear thick solution with a light yellow color was produced. The solution was diluted with water to about 5 wt. % and neutralized with 2M HCl solution to a pH of 3.5. Then, more distilled water was added to produce a 1.0 wt. % solution of polyethylene glycol based cationic quaternary ammonium (formulation A).

Figure 3A:
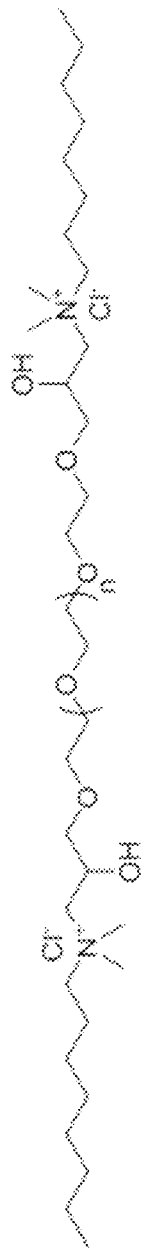
FIG. 3(A) and FIG. 3(B) shows the MS spectra of PEG-QA with (A) and without chloride (B) as detected by MS/MS.
Figure 3A:
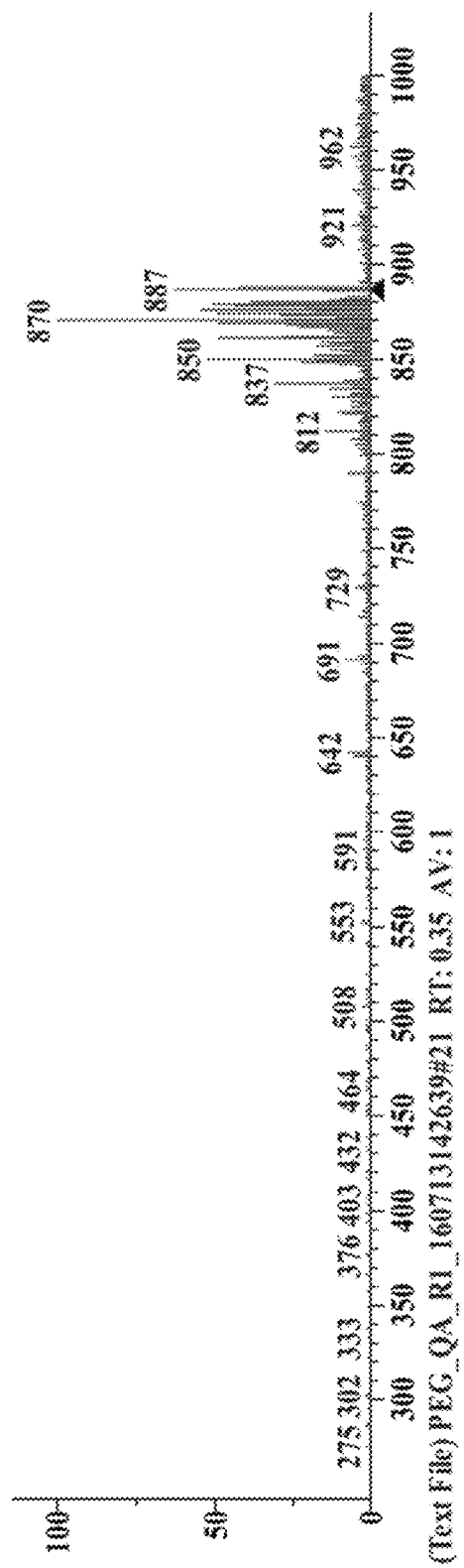
Figure 3B:
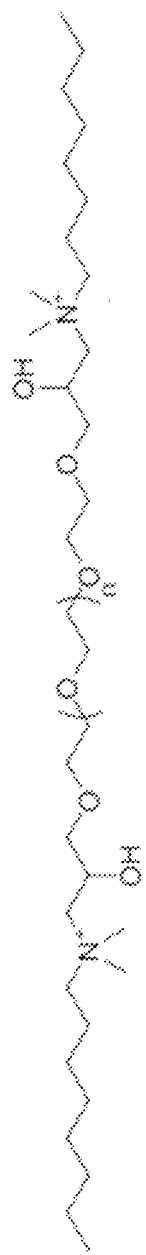
Figure 3B:
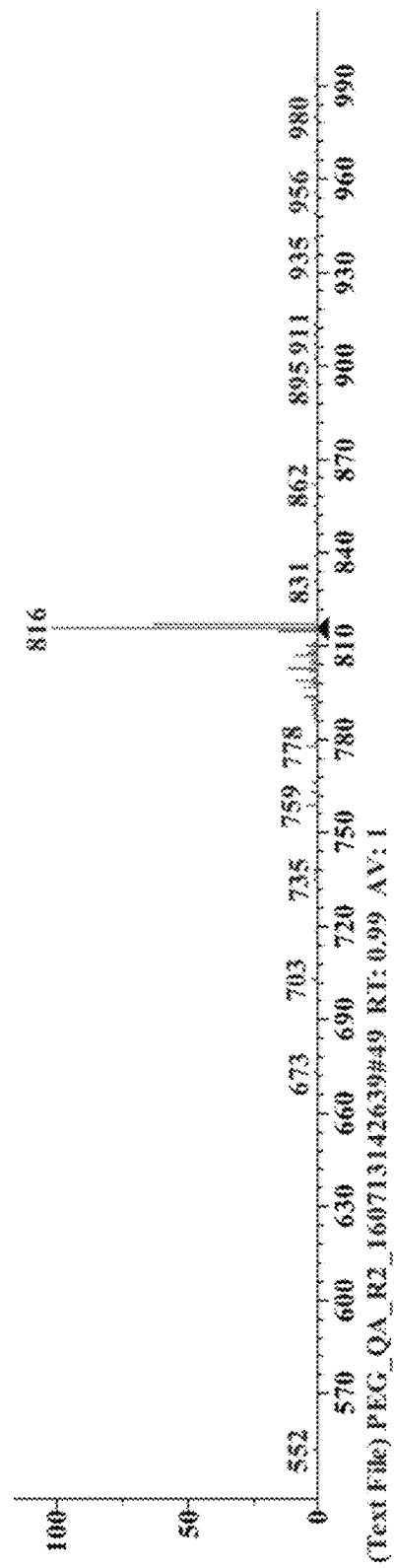

The molar mass of the prepared PEG-QA was confirmed by LC-MS (LCQ Fleet, ThermoFisher Scientific, San Jose, Calif., USA). FIG. 3(A) and FIG. 3(B) shows the MS spectra of PEG-QA with (A) and without chloride (B) as detected by MS/MS.

Preparation of Bifunctional Reagent Polypropylene Glycol Based Cationic Quaternary Ammonium (PPG-QA).

To polypropylene glycol diglycidyl ether (110.0 g, 0.172 mol, MW of PPGDGE=640 g/mol)) in around bottom flask (500 mL) was added N,N-dimethyl-n-octylamine (0.33 mol, 51.81 g). The produced solution was mixed overnight at room temperature. A clear gel with a light yellow color was produced. The gel was diluted with water to about 5 wt. % and neutralized with 2M HCl solution to a pH of 3.5. Then, more distilled water was added to produce a 1 wt. % solution of polypropylene glycol based cationic quaternary ammonium (formulation B).

Figure 4A:
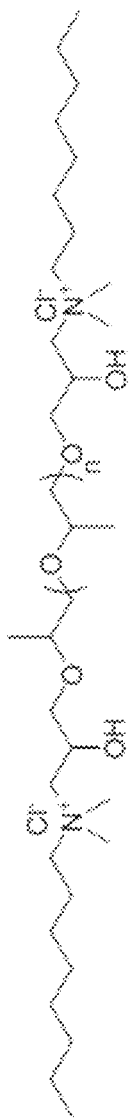
FIG. 4(A) and FIG. 4(B) show the MS spectra of PPG-QA with (A) and without chloride (B) as detected by MS/MS.
Figure 4B:
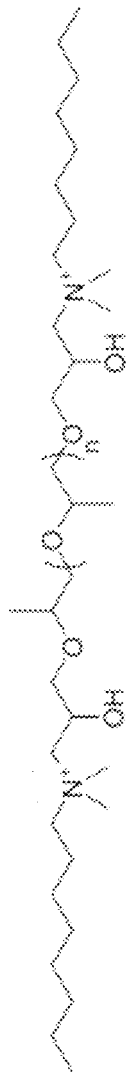
Figure 4B:
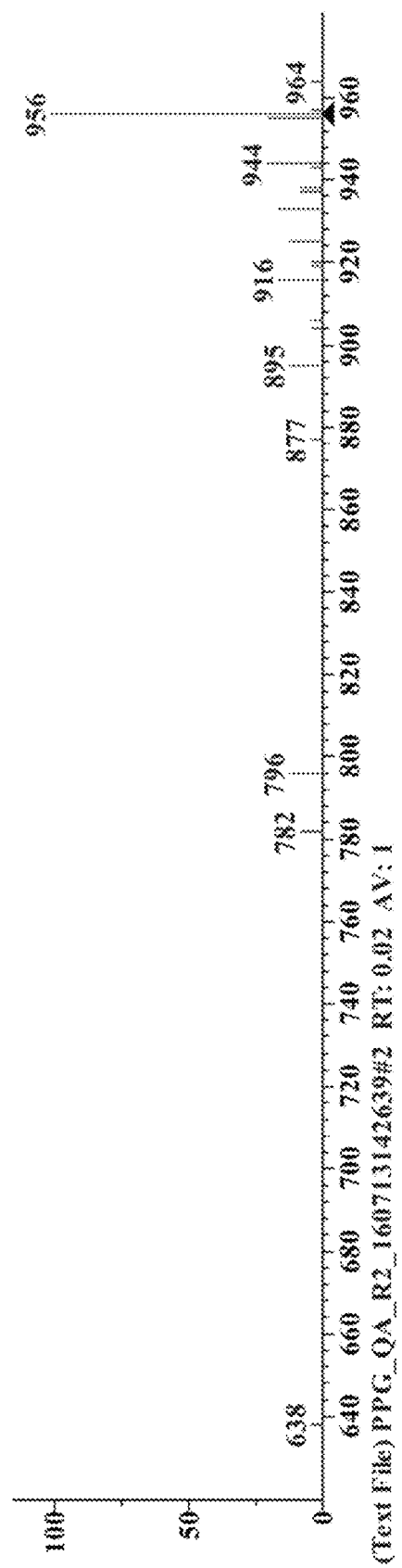

The molar mass of the prepared PPG-QA was confirmed by LC-MS (LCQ Fleet, ThermoFisher Scientific, San Jose, Calif., USA). FIG. 4(A) and FIG. 4(B) show the MS spectra of PPG-QA with (A) and without chloride (B) as detected by MS/MS.

Preparation of Bifunctional Reagent from Polypropylene Glycol Diglycidyl Ether and N-methyl-n-octylamine.

To polypropylene glycol diglycidyl ether (110.0 g, 0.172 mol, MW of PPGDGE=640 g/mol)) in around bottom flask (500 mL) was added N-methyl-n-octylamine (0.33 mol, 47.2 g). The produced solution was mixed overnight at room temperature. A clear gel with a light yellow color was produced. The gel was diluted with water to about 5 wt. % and neutralized with 2M HCl solution to a pH of 5.3. Then more distilled water was added to produce a 1 wt. % solution of polypropylene glycol based cationic quaternary ammonium (formulation C).

Preparation of Bifunctional Reagent from Polyethylene Glycol Diglycidyl Ether and N-methyl-n-octylamine:

To polyethylene glycol diglycidyl ether (110.0 g, 0.22 mol, MW of PEGDGE=500 g/mol)) in around bottom flask (500 mL) was added N-methyl-n-octylamine (0.42 mol, 60.1 g). The produced solution was mixed overnight at room temperature. A clear gel with a light yellow color was produced. The gel was diluted with water to about 5 wt. % and neutralized with 2M HCl solution to a pH of 3.5. Then more distilled water was added to produce a 1 wt. % solution of polyethylene glycol based cationic quaternary ammonium (formulation D).

EXPERIMENTAL EXAMPLES

Examples 1 to 3 illustrates a representative method for making a solution of bifunctional reagent of an embodiment of the present invention and use it in making transfer fibers in sheet form using the impregnation technique.

Example 1

Preparation of Hand sheets of Dual Functional Pulp

In this example the formulations A, B, C and D were applied to sheets of Rayfloc-JLDE (commercially available from Rayonier Advanced Materials, Jesup, Ga.) having basis weight of 640 gsm by the dip and nip process. A sample of one of the formulation were added to a plastic tray, a sheet of Rayfloc-JLDE (12×12 inch$^2$, basis weight 680 gsm) was dipped in the solution then pressed to achieve the desired level of bifunctional reagent on pulp (0.1 to 0.5 wt. %). Several sheets were prepared in the same manner, dried at 105° C.

Figure 5:
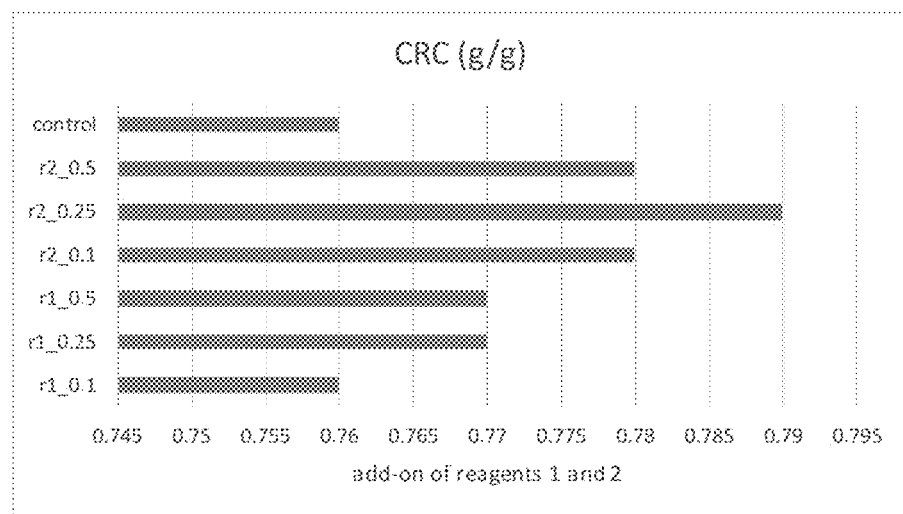
FIG. 5 shows the Centrifuge retention capacity of a dual functional pulp prepared according to Example 1.
Figure 6:
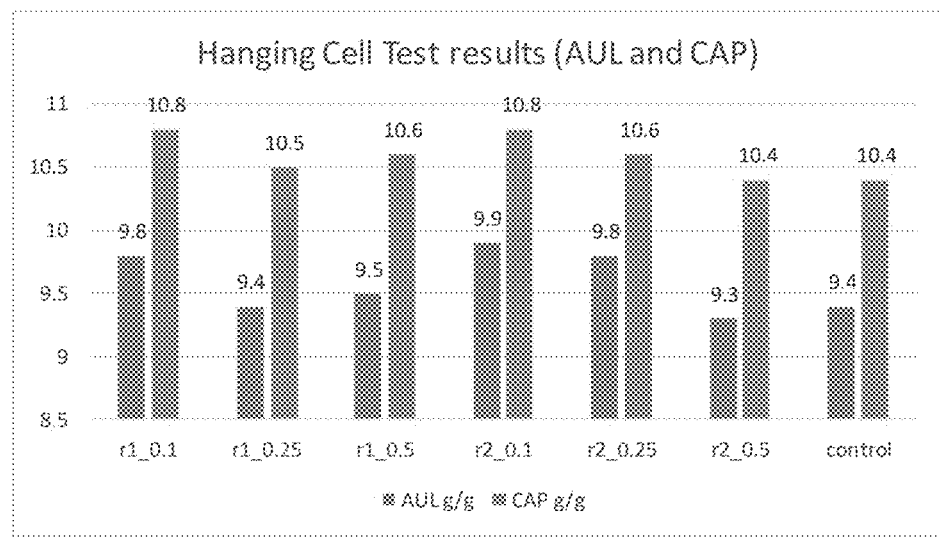
FIG. 6 shows the Absorbency under load and absorbent capacity of a dual functional pulp prepared according to Example 1.
Figure 7:
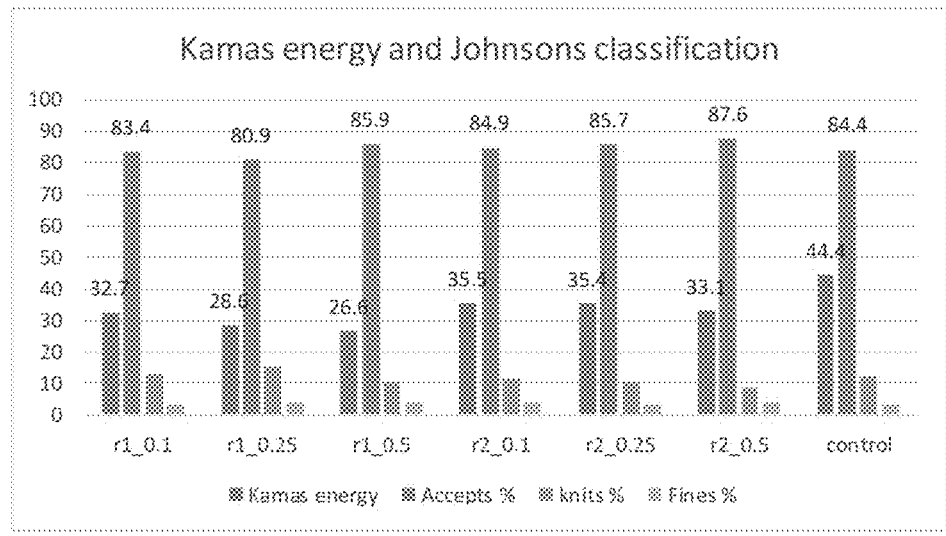
FIG. 7 shows the Kamas energy and Johnson classification of a dual functional pulp prepared according to Example 1.

Prepared sheets of specialty pulp were defiberized by feeding it through a hammer mill and evaluated for antimicrobial activities, absorbent by hanging cell test and fiber quality test. Test results are summarized in Tables I to III and in FIGS. 5 to 7. In the FIGS. 5 to 7, r1=formulation A, r2=formulation B, control: Rayfloc-JLDE.

TABLE I

Percent reduction of *Staphylococcus aureus* by dual functional fluff prepared as shown in Example 1.

| add-on of reagent (Wt. %) | Formulation | Reduction After 24 hours vs Control at T = 0 (%) |
|---|---|---|
| 0.1 | A | 0.00 |
| 0.5 | | 99.74 |
| 0.1 | B | 92.57 |
| 0.5 | | >99.92 |
| 0.25 | C | >99.93 |
| 0.25 | D | >99.93 |

TABLE II

Percent reduction of *Klebsiella pneumoniae* by dual functional pulp prepared as shown in Example 1.

| add-on of (Wt. %) | Formulation | Reduction After 24 hours vs Control at T = 0 (%) |
|---|---|---|
| 0.1 | A | 0.00 |
| 0.5 | | 99.48% |
| 0.1 | B | >99.69% |
| 0.5 | | >99.69% |
| 0.25 | C | >99.93 |
| 0.25 | D | >99.87 |

TABLE III

Percent reduction of *E. Coli* by dual functional fluff prepared as shown in Example 1.

| add-on of (Wt. %) | Formulation | Reduction After 24 hours vs Control at T = 0 (%) |
|---|---|---|
| 0.1 | A | 0.00 |
| 0.5 | | >99.69% |
| 0.1 | B | >99.69% |
| 0.5 | | >99.69% |
| 0.25 | C | >99.95 |
| 0.25 | D | >99.95 |

Example 2

Preparation of Dual Functional Pulp in Fluff Form

In this example the formulation B were applied to pulp in fluff form. Sample of the formulation B was added to a plastic container, a sample Rayfloc-JLDE with known weight in a fluff form was suspended in the solution at 4% consistency, mixed for 5 min, sheeted (12×12 inch, basis weight 680 gsm) and pressed to a 100% liquid pick up (0.1 to 0.5 wt. % of bifunctional reagent on pulp). Several sheets were prepared in the same manner, dried at 105° C.

Figure 8:
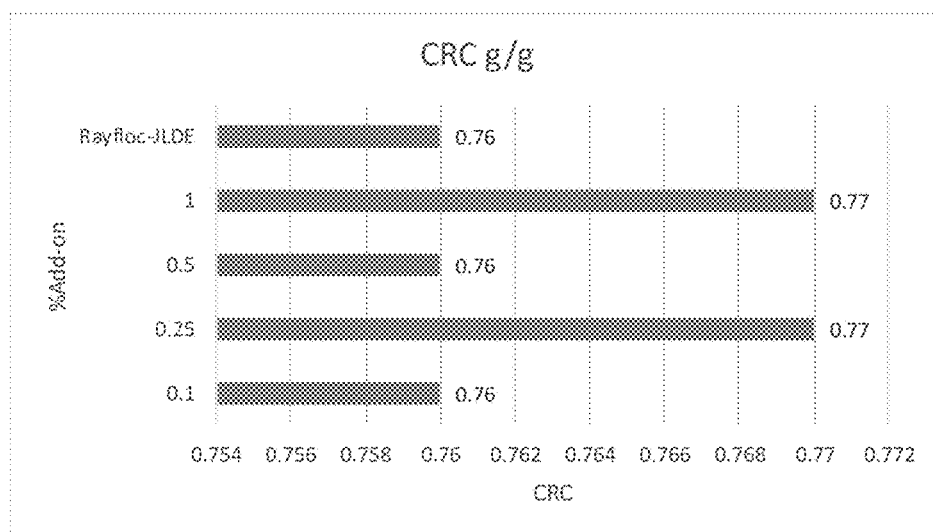
FIG. 8 shows the Centrifuge retention capacity of a dual functional pulp prepared according to Example 2 using formulation B.
Figure 9:
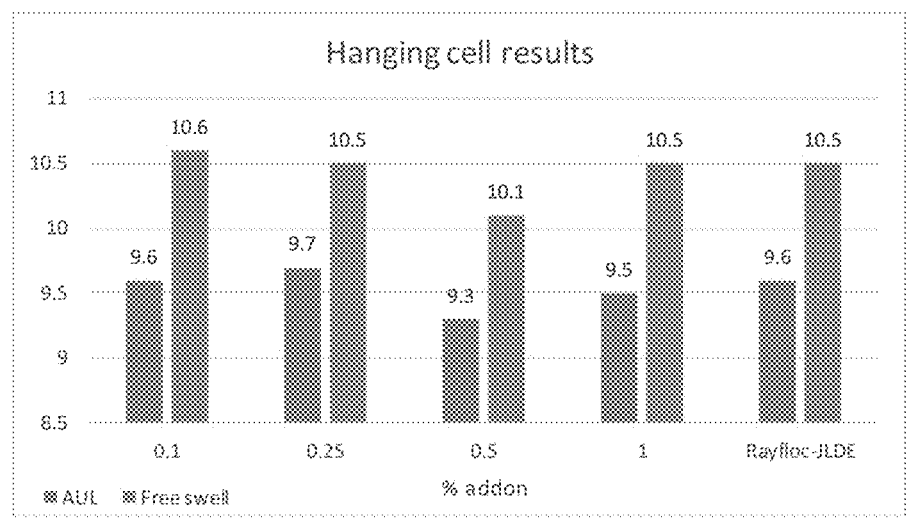
FIG. 9 shows the Absorbency under load and absorbent capacity of a dual functional pulp prepared according to Example 2 using formulation B.
Figure 10:
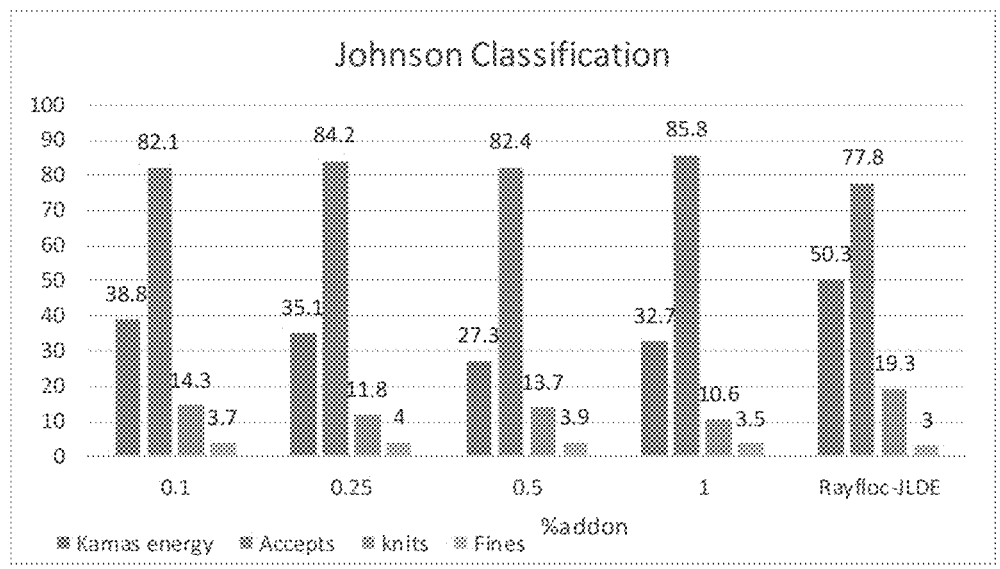
FIG. 10 shows the Kamas energy and Johnson classification of a dual functional pulp prepared according to Example 2 using formulation B.

Prepared sheets of specialty fluff were defiberized by feeding them through a hammer mill and evaluated for antimicrobial activities, absorbent by hanging cell test and fiber quality test. Test results are summarized in Table IV and in FIGS. 8 to 10.

TABLE IV

Percent reduction of three microbial cells by dual functional pulp prepared as shown in example 2 using formulation B.

| add-on of (Wt. %) of PEG-QA reagent | Bacterial cell | Reduction After 24 hours vs Control at T = 0 (%) |
|---|---|---|
| 0.5 | Staphylococcus | 99.62% |
| 1.0 | aureus | >99.99% |
| 0.5 | Klebsiella | >99.69 |
| 1 | pneumoniae | >99.99 |
| 0.5 | E. coli | >99.69 |
| 1 |  | >99.99 |

Burst Index

Figure 11:
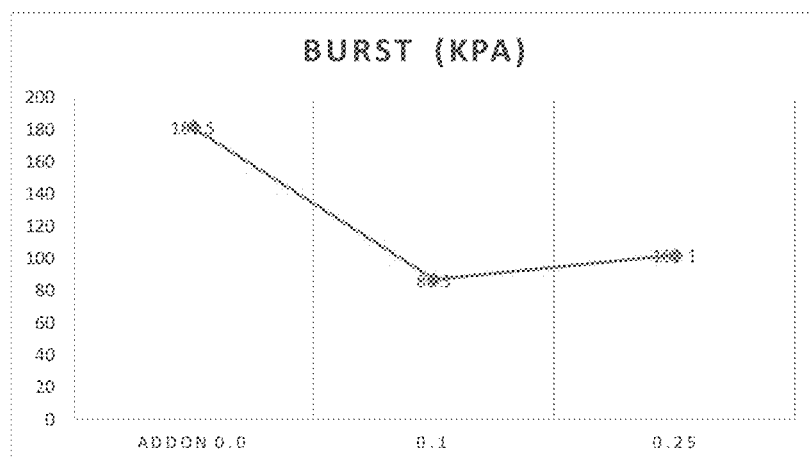
FIG. 11 shows the Burst results of a dual functional pulp for sheet with 100 gsm.

Sheets with circular shape and basis weights of about 85 gsm (diameter=15.8 cm) were prepared according to TAPPI method T202 sp-02. Prepared sheet were conditioned according to TAPPI T 402 (23.0±1° C., 50.0±2% relative humidity). The burst and burst index were determined according to TAPPI method T403 using Bursting Strength Tester BT-10 model (Techlab System, TLS). Results are summarized in FIG. 11.

Referring to Tables above and Figures, Tables I to IV show the activities of the bifunctional reagents against three bacteria strains, two gram negative and one gram positive. The results shown in the Tables I to IV are collected after 24 hr of contact between the pulp and the bacteria strains. The results show that, the PPG-QA reagent exhibited high activity at a very low add-on of 0.1 wt. % against the three strains.

The other reagent PEG-QA exhibited excellent activity against the three tested strains at higher add-on of 0.5 wt. %. Both reagents eliminated and stopped the growth of bacteria during the testing period of 24 hr.

For the commercial de-bonding reagent in order to be effective a high add-on is required, and they negatively affect the absorbent properties of the treated pulp. In contrast to that, the reagents of current invention as demonstrated in FIGS. 5 to 11 showed good performance even at low add-on, as low as 0.1 wt. %. At 0.1 wt. % the Kamas energy was decreased by more than 26.0% and the burst was decreased by more than 50%. The absorbent properties of the specialty pulp are also not affected by treatment with the bifunctional reagents of the present invention. The results demonstrate that the specialty fluff pulp has the same or higher CRC, AUL, and CAP as conventional fluff pulp.

The invention claimed is:

1. A bifunctional reagent comprising a reaction product of an alkyl amine and an epoxide, wherein the bifunctional reagent has the following chemical structure:

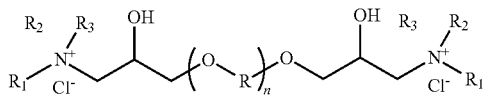

wherein n is an integer from 1 to 1,000;

R is ethyl, isopropyl or butyl;

$R_1$, and $R_2$, can be the same or different and are selected from hydrogen, methyl, or ethyl; and $R_3$, is an alkyl group with 3 to 30 carbon atoms, which alkyl group may be saturated, unsaturated, substituted, un-substituted, branched, un-branched, cyclic, and/or acyclic, and may contain 1 to 3 heteroatoms.

2. The bifunctional reagent of claim 1, wherein the bifunctional reagent is terminated with β-hydroxyl quaternary ammonium groups.

3. The bifunctional reagent of claim 1, wherein the alkyl amine is selected from N,N-dimethylethylamine, N,N-dimethylpropyl amine, N,N-dimethylbutylamine, N,N-dimethylpentylamine, N,N-dimethylhexylamine, N,N-dimethyloctylamine, N-methyl-n-octyl amine and n-octylamine.

4. The bifunctional reagent of claim 1, which is soluble or forms a suspension in water.

5. A cellulose composition, comprising cellulose fibers and about 0.01 wt. % to about 1.0 wt. % of the bifunctional reagent of claim 1.

6. The cellulose composition of claim 5, which has antimicrobial activity.

7. The cellulose composition of claim 5, which reduces, when dosed with a bacteria suspension, the number of bacteria by more than 95% within a period of 24 hr.

8. The cellulose composition of claim 5, which prevents, when dosed with a bacteria suspension, bacteria growth for up to about 36 hours.

9. The cellulose composition of claim 6, wherein the bacteria is gram positive or gram negative.

10. The cellulose composition of claim 6, wherein the bacteria is Proteus mirabilis, Staphylococcus aureus, Klebsiella pneumonia or E. coli.

11. The cellulose composition of claim 5, wherein the cellulose composition having 0.1 wt. % bifunctional reagent has a Kamas energy which is reduced at least 15% compared to the Kamas energy of a cellulose composition without the bifunctional reagent.

12. The cellulose composition of claim 5, wherein the cellulose composition having 0.1 wt. % bifunctional reagent has a Kamas energy which is reduced at least 25% compared to the Kamas energy of a cellulose composition without the bifunctional reagent.

13. The cellulose composition of claim 5, wherein the cellulose composition having 0.1 wt. % bifunctional reagent in sheet form with a 100 gsm has a burst index which is reduced by at least 15% compared to the burst index of a cellulose composition without the bifunctional reagent.

14. The cellulose composition of claim 5, wherein the cellulose composition having 0.25 wt. % bifunctional reagent in sheet form with a 100 gsm has a burst index which is reduced by at least 25% compared to the burst index of a cellulose composition without the bifunctional reagent.

15. An absorbent article of manufacture, comprising the cellulose composition of claim 5.

16. The absorbent article of claim 15, which is a diaper, an incontinent device, a feminine hygiene product, a wipe, a bandage, a bed pad, or any combination thereof.

17. The bifunctional reagent of claim 1, wherein n is an integer from 1 to 100.

18. The bifunctional reagent of claim 1, wherein R is ethyl or isopropyl.

19. The bifunctional reagent of claim 1, wherein at least one of $R_1$, and $R_2$ is methyl.

20. The bifunctional reagent of claim 1, wherein $R_3$ is an alkyl group with 3 to 20 carbon atoms.

* * * * *